United States Patent
Arjomand et al.

(10) Patent No.: US 8,373,114 B2
(45) Date of Patent: Feb. 12, 2013

(54) TOTAL CARBON MASS DETERMINATION BY ACCELERATOR MASS SPECTROMETRY (AMS) USING 13C ISOTOPE DILUTION

(75) Inventors: Ali Arjomand, Medina, WA (US); Ugo Zoppi, Auburn, WA (US); James Crye, Seattle, WA (US)

(73) Assignee: Accium Biosciences, Seattle, WA (US)

( * ) Notice: Subject to any disclaimer, the term of this patent is extended or adjusted under 35 U.S.C. 154(b) by 462 days.

(21) Appl. No.: 12/559,470

(22) Filed: Sep. 14, 2009

(65) Prior Publication Data
US 2010/0264305 A1 Oct. 21, 2010

Related U.S. Application Data

(60) Provisional application No. 61/097,212, filed on Sep. 15, 2008.

(51) Int. Cl.
*B01D 59/44* (2006.01)
(52) U.S. Cl. ........ 250/282; 250/281; 250/283; 250/288; 436/518
(58) Field of Classification Search .......... 250/281–283, 250/288; 436/518
See application file for complete search history.

(56) References Cited

U.S. PATENT DOCUMENTS

| | | | |
|---|---|---|---|
| 5,209,919 A * | 5/1993 | Turteltaub et al. | 424/1.11 |
| 5,661,299 A * | 8/1997 | Purser | 250/281 |
| 7,985,589 B2 * | 7/2011 | Garner et al. | 436/8 |
| 2006/0194341 A1 * | 8/2006 | Garner et al. | 436/518 |
| 2007/0018091 A1 * | 1/2007 | Garner et al. | 250/283 |
| 2007/0215814 A1 * | 9/2007 | Kitchen | 250/397 |
| 2010/0120156 A1 * | 5/2010 | Garner et al. | 436/8 |
| 2010/0235934 A1 * | 9/2010 | Friedman et al. | 800/13 |

OTHER PUBLICATIONS

Zoppi et al. "Performance evaluation of the new AMS system at Accium Biosciences" Radiocarbon, vol. 49, NR 1, 2007, p. 171-180.*

* cited by examiner

*Primary Examiner* — Michael Logie
(74) *Attorney, Agent, or Firm* — Jeffrey B. Oster

(57) ABSTRACT

There is disclosed a method for direct quantitation of total carbon and $^{14}C/^{12}C$ ratios in a single measurement using Accelerator Mass Spectrometry (AMS). More specifically, measurement of both total carbon and $^{14}C/^{12}C$ ratio is performed in the same sample at the same time. The disclosed method provides improved sensitivity and accuracy for reliably calculating $^{14}C$-labeled compound concentrations in biological samples. There is also a reduction in measurement time, sample volume requirement and measurement cost compared to existing procedures.

3 Claims, 2 Drawing Sheets

TOTAL CARBON MASS DETERMINATION BY ACCELERATOR MASS SPECTROMETRY (AMS) USING 13C ISOTOPE DILUTION

CROSS REFERENCE TO RELATED APPLICATION

This disclosure claims priority to U.S. Provisional Patent Application 61/097,212 filed 15 Sep. 2008.

TECHNICAL FIELD

The present disclosure provides a method for direct quantitation of total carbon and $^{14}C/^{12}C$ ratios in a single measurement using Accelerator Mass Spectrometry (AMS). More specifically, measurement of both total carbon and $^{14}C/^{12}C$ ratio is performed in the same sample at the same time. The disclosed method provides improved sensitivity and accuracy for reliably calculating $^{14}C$-labeled compound concentrations in biological samples. There is also a reduction in measurement time, sample volume requirement and measurement cost compared to existing procedures.

BACKGROUND

Accelerator Mass Spectrometry (AMS) is a type of isotope ratio mass spectrometry (IRMS) developed in the 1970s to directly count individual ions of very rare isotopes. AMS is an extremely sensitive method for detecting isotopes having concentrations of parts per billion to parts per quintillion. Recently, dedicated AMS instruments have been developed for quantifying radioisotopes that are particularly suitable for pharmaceutical research, particularly $^{14}C$, at natural concentrations (Vogel, (2005). "Accelerator mass spectrometry for quantitative in vivo tracing" BioTechniques 38:S25-S29, 2005; Nelson et al., 1977 "Carbon-14: direct detection at natural concentrations" Science 198:507-508; and Bennett et al., 1977 "Radiocarbon dating using electrostatic accelerators: negative-ions provide key" Science 198:508-510). In practice, AMS traces very low doses of compounds (micrograms) using extremely low radiation (<100 nanoCurie) in animal models and human subject. Some of the common clinical applications of AMS are quantitation of drug concentration in pharmacokinetic, mass balance, absolute bioavailability, microdosing, and metabolite profiling studies.

AMS is used when extreme sensitivity is required for early stage drug development. AMS quantifies the amount of radiocarbon-labeled compound in a biological sample with attomole ($10^{-18}$M) sensitivity. Traditional Liquid Scintillation Counting (LSC) methods only count the isotopes that decay during the detection period. In contrast, AMS counts every radioisotope present in the sample, whether it decays or not. Since radiocarbon is relatively stable (i.e., approximately 5,730 year half-life), there is a $10^6$-fold increase in the sensitivity of AMS compared to LSC.

AMS instruments accelerate ions to million electron volt energies where molecular isobars are destroyed yielding ions of sufficient energy for identification by characteristic interactions with nuclear particle detectors. An AMS instrument produces a beam of C-ions by bombarding the cool cesiated surface of a graphite sample with about 5 keV Cs+ ions. The C-beam produced by the sputtering of the sample by the Cs+ beam is accelerated, focused, and mass analyzed into mass 14, and 13 amu beams. Samples are measured with 0.3% precision and accuracy, machine background levels are consistently in the low $10^{-16}$($^{14}C/^{12}C$), and chemical background are approximately equivalent to a fraction of modern of 0.004. In addition, when 100-times-modern samples are processed, no increase in background is observed, either during sample processing or during AMS measurement. This corresponds to a dynamic range for $^{14}C$ analysis of 6 orders of magnitude (Zoppi et al., "Performance Evaluation of New Accelerator Mass Spectrometer at Accium BioSciences", Radiocarbon, 49:171-180, 2007).

An AMS instrument generates $^{14}C/^{12}C$ ratios in a given graphite sample. The graphite is produced separately from a small amount of plasma, urine, tissue homogenate or fecal blend, for example. The absolute concentration of $^{14}C$ in these samples is calculated by multiplying the $^{14}C/^{12}C$ ratio by the total amount of carbon in that sample. For example, the AMS ratio (commonly DPM/g carbon) is multiplied by 0.040 g carbon/mL plasma to produce the absolute $^{14}C$ concentration (DPM/mL plasma). It is, therefore, required to determine the concentration of carbon in biological samples in order to perform this calculation. There are two approaches for this:

(1) Determine the carbon concentration empirically in every sample, for example, the total carbon concentration in each sample (75-100 μL) is measured by freezing the sample over liquid nitrogen in individual Costech tin capsules (Ventura, Calif.) followed by overnight lyophilization. Each capsule is then placed inside a second tin capsule, rolled into a ball and analyzed for total carbon concentration using a Carlo-Erba carbon analyzer (Pella, "Elemental organic analysis" Am Lab 22:116-25, 1990). Alternatively, total organic carbon is determined using powerful oxidation via the combination of sodium persulphate and UV oxidation at 80° C. This approach ensures that all dissolved carbon species will be detected. Highly sensitive infra-red detectors detect extremely low concentrations of carbon with excellent reproducibility in the low parts-per-billion (ppb) range.

(2) Use a reference value for carbon concentration without measuring the actual concentration in individual samples.

The second approach is suitable in samples that have consistent carbon concentration across the population and over time. Plasma samples are amenable for this approach as there is little variation in the overall carbon concentration across the population and over time. In other samples, such as urine and tissue or fecal blends, there is considerable variation in the carbon concentration across the population and over time. The carbon concentration in these samples needs to be determined empirically for accurate calculation of the absolute $^{14}C$ concentration (FIG. 1 and FIG. 2).

One of the more common applications of AMS is to support clinical studies during early phase drug development. A typical mass balance study produces over 200 plasma samples, 150 urine samples and 100 fecal samples. All of the samples have to be converted to graphite prior to AMS measurement. In addition, the urine and fecal blends have to be processed separately for quantitation of total carbon concentration. This adds significant cost to the study and prolongs the release of the analytical report.

It would be advantageous and there is a need in the art to complete these clinical studies in a more rapid and cost-effective manner. The disclosed method addresses this need in the art.

SUMMARY

The present disclosure provides a method for simultaneous quantitation of both $^{14}C/^{12}C$ ratios and total carbon of graphitized samples of unknown mass on a single AMS instrument, comprising:

(a) adding a known amount of carbon carrier with predetermined $^{13}C/^{12}C$ and $^{14}C/^{13}C$ ratios to the test sample to form a mix;
(b) measuring the mix by AMS to determine $^{13}C/^{12}C$ and $^{14}C/^{13}C$ ratios;
(c) determining the mass and the $^{14}C$ concentration of the test sample Preferably, the $^{13}C/^{12}C$ and $^{14}C/^{13}C$ ratios are measured according to the formula:

$$\boxed{\left(\frac{13}{12}\right)_S, \left(\frac{14}{13}\right)_S, M_S} + \boxed{\left(\frac{13}{12}\right)_C, \left(\frac{14}{13}\right)_C, M_C} = \boxed{\left(\frac{13}{12}\right)_M, \left(\frac{14}{13}\right)_M, M_M}$$

Sample     Carbon Carrier     Mix wherein masses ($M_S$ for sample mass, $M_C$ for carbon carrier mass and $M_M$ for the determined mix mass) and number of atoms are added:

$$M_M = M_S + M_C$$

$$12_M = 12_S + 12_C$$

$$13_M = 13_S + 13_C$$

$$14_M = 14_S + 14_C.$$

Preferably, for isotopic ratios, $M_{12}$ and $M_{13}$ are the atomic masses of $^{12}C$ and $^{13}C$ respectively, then:

$$M_{S,C} = 12_{S,C} M_{12} + 13_{S,C} M_{13}$$
$$= 12_{S,C}\left(M_{12} + \left(\frac{13}{12}\right)_{S,C} M_{13}\right) \equiv 12_{S,C} K_{S,C}$$

and the $^{13}C/^{12}C$ of the mixture is given by:

$$\left(\frac{13}{12}\right)_M = \frac{13_S + 13_C}{12_S + 12_C}$$
$$= \frac{\left(\frac{13}{12}\right)_S 12_S + \left(\frac{13}{12}\right)_C 12_C}{12_S + 12_C}$$
$$= \frac{\frac{M_S}{K_S}\left(\frac{13}{12}\right)_S + \frac{M_C}{K_C}\left(\frac{13}{12}\right)_C}{\frac{M_S}{K_S} + \frac{M_C}{K_C}}.$$

DETAILED DESCRIPTION

Figure 1:
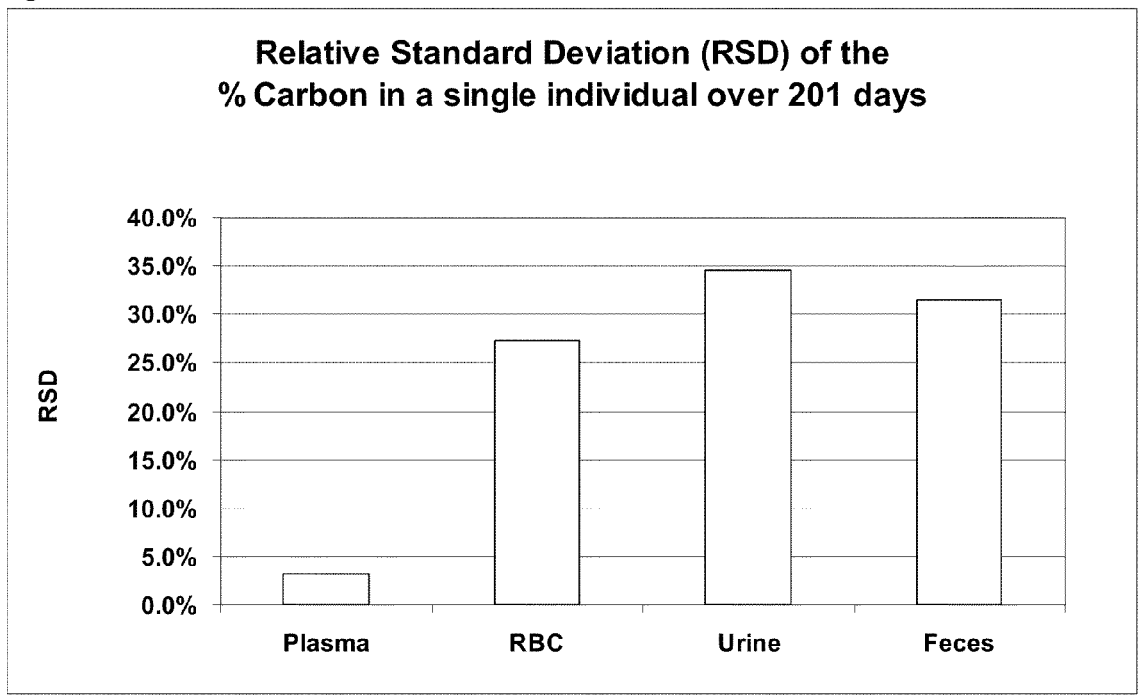
FIG. 1 shows the relative standard deviation of the % carbon in plasma, red blood cells (RBC), urine and feces from a single individual over a 201 day period.
Figure 2:
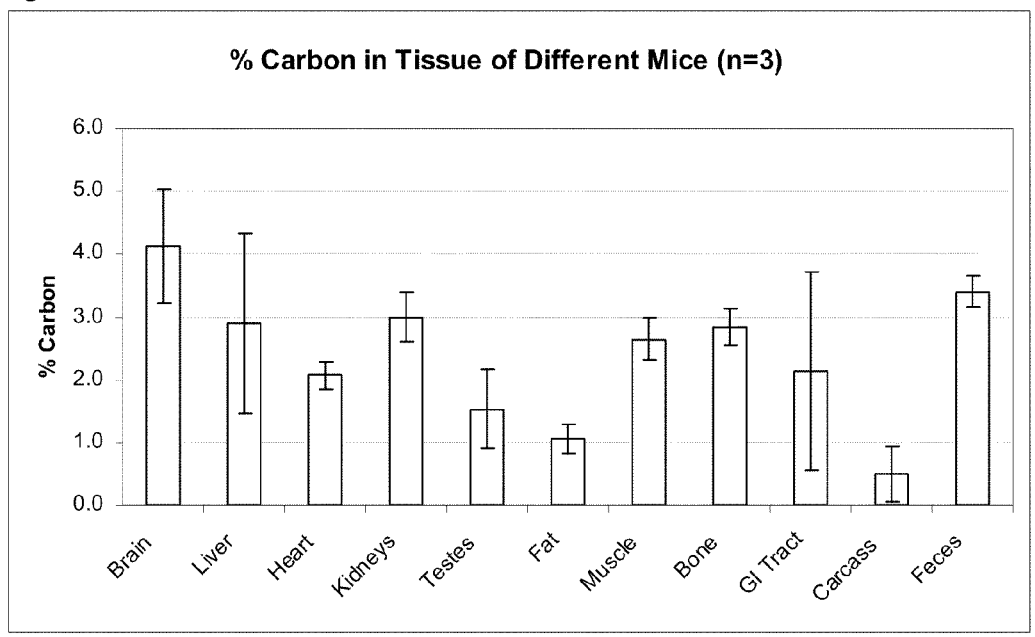
FIG. 2 shows the variation in the % carbon of various tissues and excreta obtained from mice (n=3).

The disclosed method eliminates the need to separately quantify the total carbon concentration. The disclosed method also provides a more accurate quantitation of $^{14}C$ concentration because the total carbon concentration is determined in the same sample aliquot as the $^{14}C/^{12}C$ determination. Previous approaches require two separate aliquots of the sample, one for the AMS graphite and one for the total carbon determination. In samples that are not completely homogenous, such as fecal blends, there is a risk that each aliquot may provide a representative sample of the blend, resulting in inconsistent determination of $^{14}C/^{12}C$ and total carbon. The disclosed method eliminates this possibility by using a single aliquot for determination of both $14C/^{12}C$ and total carbon.

A known amount of carbon carrier with predetermined $^{13}C/^{12}C$ and $^{14}C/^{13}C$ ratios is added to a sample of unknown mass. By measuring by AMS the $^{13}C/^{12}C$ and $^{14}C/^{13}C$ ratios of the mix it is possible to determine the mass and the $^{14}C$ concentration of the original sample:

$$\boxed{\left(\frac{13}{12}\right)_S, \left(\frac{14}{13}\right)_S, M_S} + \boxed{\left(\frac{13}{12}\right)_C, \left(\frac{14}{13}\right)_C, M_C} = \boxed{\left(\frac{13}{12}\right)_M, \left(\frac{14}{13}\right)_M, M_M}$$

Sample     Carbon Carrier     Mix

Masses and number of atoms can be simply added:

$$M_M = M_S + M_C$$

$$12_M = 12_S + 12_C$$

$$13_M = 13_S + 13_C$$

$$14_M = 14_S + 14_C$$

For isotopic ratios, the procedure is modified. If $M_{12}$ and $M_{13}$ are the atomic masses of $^{12}C$ and $^{13}C$ respectively, then:

$$M_{S,C} = 12_{S,C} M_{12} + 13_{S,C} M_{13}$$
$$= 12_{S,C}\left(M_{12} + \left(\frac{13}{12}\right)_{S,C} M_{13}\right) \equiv 12_{S,C} K_{S,C}$$

The $^{13}C/^{12}C$ of the mixture is given by:

$$\left(\frac{13}{12}\right)_M = \frac{13_S + 13_C}{12_S + 12_C}$$
$$= \frac{\left(\frac{13}{12}\right)_S 12_S + \left(\frac{13}{12}\right)_C 12_C}{12_S + 12_C}$$
$$= \frac{\frac{M_S}{K_S}\left(\frac{13}{12}\right)_S + \frac{M_C}{K_C}\left(\frac{13}{12}\right)_C}{\frac{M_S}{K_S} + \frac{M_C}{K_C}}.$$

Similarly, $$\left(\frac{14}{13}\right)_M = \frac{14_S + 14_C}{13_S + 13_C}$$
$$= \frac{\left(\frac{14}{13}\right)_S\left(\frac{13}{12}\right)_S 12_S + \left(\frac{14}{13}\right)_C\left(\frac{13}{12}\right)_C 12_C}{\left(\frac{13}{12}\right)_S 12_S + \left(\frac{13}{12}\right)_C 12_C}$$

-continued $$= \frac{\frac{M_S}{K_S}\left(\frac{14}{13}\right)_S\left(\frac{13}{12}\right)_S + \frac{M_C}{K_C}\left(\frac{14}{13}\right)_C\left(\frac{13}{12}\right)_C}{\left(\frac{13}{12}\right)_S\frac{M_S}{K_S} + \left(\frac{13}{12}\right)_C\frac{M_C}{K_C}}$$

These last 2 equation can be solved to find expressions for $M_S$ and $(14/13)_S$. It can be demonstrated that:

$$M_S = M_C \cdot \frac{W_S}{W_C} \cdot \frac{\left(\frac{13}{12}\right)_C - \left(\frac{13}{12}\right)_M}{\left(\frac{13}{12}\right)_M - \left(\frac{13}{12}\right)_S}$$

and $$\left(\frac{14}{13}\right)_S = \left(\frac{14}{13}\right)_M + \frac{\left(\frac{13}{12}\right)_C}{\left(\frac{13}{12}\right)_S} \cdot \frac{\left(\frac{13}{12}\right)_M - \left(\frac{13}{12}\right)_S}{\left(\frac{13}{12}\right)_C - \left(\frac{13}{12}\right)_M} \cdot \left[\left(\frac{14}{13}\right)_M - \left(\frac{14}{13}\right)_C\right]$$

$(14/13)_C$, $(13/12)_C$, $(14/13)_M$ and $(13/12)_M$ are measured by AMS. To be able to calculate $M_S$ and $(14/13)_S$ an estimated value for $(13/12)_S$ is used based on the natural abundance $^{13}C$.

The formula for $(^{14}C/^{13}C)$ does not depend on the amount of carbon carrier used and thus is not affected by its uncertainty.

EXPERIMENTAL RESULTS

Using commercially available [1-$^{13}$C]glucose ($C_6H_{12}O_6$ with one carbon atom enriched to 99% $^{13}$C) a solution 'A' having a $^{13}C/^{12}C$ ratio of approximately 4% was produced. Four additional samples were then prepared by mixing 5 μl of this solution with different known amount of IAEA-C6 (sucrose) standard.

Figure 3:
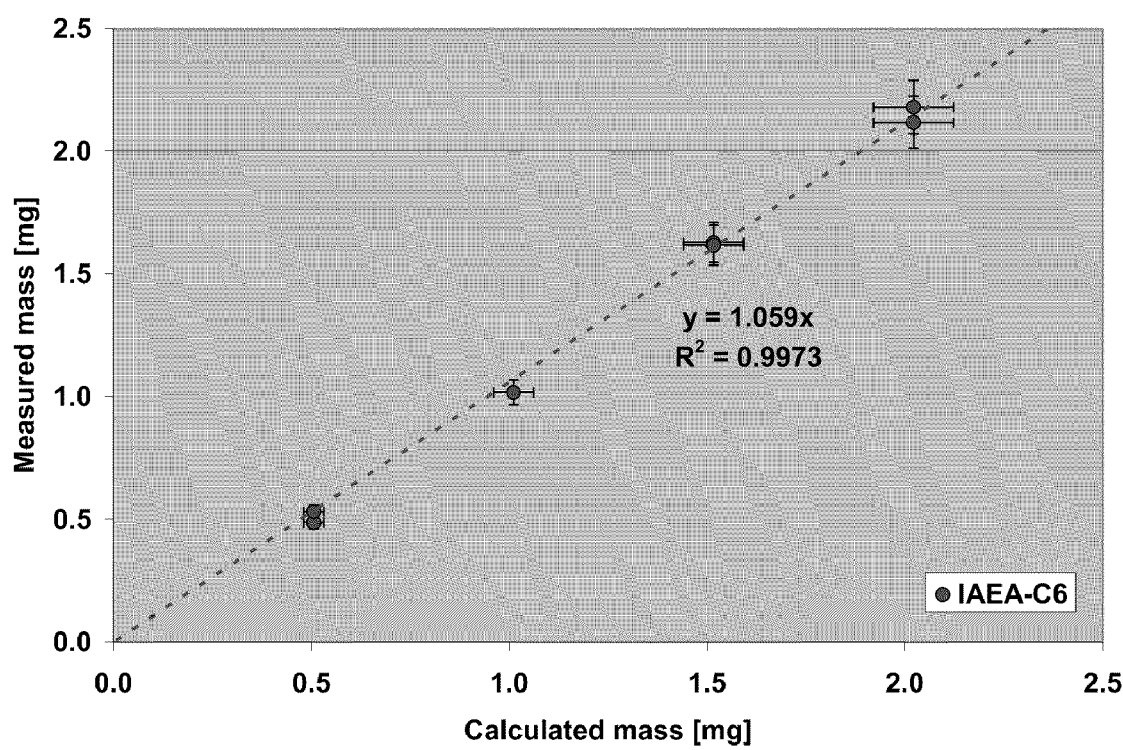
FIG. 3 shows the carbon mass of the C6 component compared to the calculated values. Particularly, the carbon masses were determined to be within 5% of the correct value, with very good linearity ($R^2 = 0.997$).

By measuring the $^{13}C/^{12}C$ ratios of all these samples ('A' solution and 'A'/C6 mixtures) we were able, for each 'A'/C6 mixture, to determine the carbon mass of the C6 component and compare it to the calculated values shown in Table 1 below and graphically in FIG. 3:

TABLE 1

| Calculated Mass | Measured Mass |
|---|---|
| 0.51 mg | 0.49 mg |
| 0.51 mg | 0.53 mg |
| 1.01 mg | 1.02 mg |
| 1.52 mg | 1.63 mg |
| 1.52 mg | 1.62 mg |
| 2.02 mg | 2.12 mg |
| 2.02 mg | 2.18 mg |

We were able to determine the carbon masses within 5% of the correct value. The very good linearity ($R^2$=0.997) indicates that the coefficient of 1.059 might be due to a systematic error that might be present. Without being bound by theory, this likely was caused by the fact that the $^{13}C/^{12}C$ ratio of the 'A' solution (around 4%) was normalized using C6 samples at natural abundance (1.11%). This problem can be overcome by using a certified $^{13}C/^{12}C$ standard with a ratio of approximately 6%.

We claim:

1. A method for simultaneous quantitation of both $^{14}C/^{12}C$ ratios and total carbon of graphitized samples of unknown mass on a single AMS instrument, comprising:
   (a) adding a known amount of carbon carrier with predetermined $^{13}C/^{12}C$ and $^{14}C/^{13}C$ ratios to a test sample to form a mix;
   (b) measuring the mix by AMS to determine $^{13}C/^{12}C$ and $^{14}C/^{13}C$ ratios; and
   (c) determining the mass and the $^{14}C$ concentration of the test sample.

2. The method for simultaneous quantitation of both $^{14}C/^{12}C$ ratios and total carbon of graphitized samples of unknown mass on a single AMS instrument of claim 1, wherein the $^{13}C/^{12}C$ and $^{14}C/^{13}C$ ratios are measured according to the formula:

$$\boxed{\left[\left(\frac{13}{12}\right)_S, \left(\frac{14}{13}\right)_S, M_S\right]} + \boxed{\left[\left(\frac{13}{12}\right)_C, \left(\frac{14}{13}\right)_C, M_C\right]} = \boxed{\left[\left(\frac{13}{12}\right)_M, \left(\frac{14}{13}\right)_M, M_M\right]}$$

Sample     Carbon Carrier     Mix wherein masses ($M_s$ for sample mass, $M_c$ for carbon carrier mass and $M_M$ for the determined mix mass) and number of atoms are added:

$M_M = M_S + M_C$ $12_M = 12_S + 12_C$ $13_M = 13_S + 13_C$ $14_M = 14_S + 14_C$.

3. The method for simultaneous quantitation of both $^{14}C/^{12}C$ ratios and total carbon of graphitized samples of unknown mass on a single AMS instrument of claim 1, wherein for isotopic ratios, $M_{12}$ and $M_{13}$ are the atomic masses of $^{12}C$ and $^{13}C$ respectively, then:

$$M_{S,C} = 12_{S,C} M_{12} + 13_{S,C} M_{13}$$

$$= 12_{S,C}\left(M_{12} + \left(\frac{13}{12}\right)_{S,C} M_{13}\right) \equiv 12_{S,C} K_{S,C}$$

and the $^{13}C/^{12}C$ of the mixture is given by:

$$\left(\frac{13}{12}\right)_M = \frac{13_S + 13_C}{12_S + 12_C}$$

$$= \frac{\left(\frac{13}{12}\right)_S 12_S + \left(\frac{13}{12}\right)_C 12_C}{12_S + 12_C}$$

$$= \frac{\frac{M_S}{K_S}\left(\frac{13}{12}\right)_S + \frac{M_C}{K_C}\left(\frac{13}{12}\right)_C}{\frac{M_S}{K_S} + \frac{M_C}{K_C}}.$$

* * * * *